United States Patent
Olah et al.

(10) Patent No.: US 9,504,952 B2
(45) Date of Patent: Nov. 29, 2016

(54) RECYCLING CARBON DIOXIDE VIA CAPTURE AND TEMPORARY STORAGE TO PRODUCE RENEWABLE FUELS AND DERIVED PRODUCTS

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 96 days.

(21) Appl. No.: 13/877,894

(22) PCT Filed: Sep. 9, 2011

(86) PCT No.: PCT/US2011/050969
§ 371 (c)(1),
(2), (4) Date: Aug. 9, 2013

(87) PCT Pub. No.: WO2012/047443
PCT Pub. Date: Apr. 12, 2012

(65) Prior Publication Data
US 2013/0331616 A1    Dec. 12, 2013

Related U.S. Application Data

(60) Provisional application No. 61/389,482, filed on Oct. 4, 2010.

(51) Int. Cl.
| | |
|---|---|
| *B01D 53/02* | (2006.01) |
| *C07C 1/20* | (2006.01) |
| *C07C 29/151* | (2006.01) |
| *C07C 41/09* | (2006.01) |
| *C10G 3/00* | (2006.01) |
| *C01B 3/32* | (2006.01) |

(52) U.S. Cl.
CPC .............. *B01D 53/02* (2013.01); *C07C 1/20* (2013.01); *C07C 29/1518* (2013.01); *C07C 41/09* (2013.01); *C10G 3/42* (2013.01); *C01B 3/32* (2013.01); *C01B 2203/0205* (2013.01); *C01B 2203/0222* (2013.01); *C01B 2203/0233* (2013.01); *C01B 2203/06* (2013.01); *C01B 2203/061* (2013.01); *Y02C 10/08* (2013.01); *Y02E 50/18* (2013.01); *Y02P 20/133* (2015.11); *Y02P 30/10* (2015.11); *Y02P 30/42* (2015.11)

(58) Field of Classification Search
CPC ..... C07C 1/20; C07C 29/1518; C07C 41/09; C07C 11/04; C07C 11/06; C07C 31/04; C07C 43/043; B01D 53/02; C10G 3/42; Y02E 50/18; Y02E 50/00; C01B 2203/0205; C01B 2203/0222; C01B 2203/0233; C01B 2203/06; C01B 2203/061; C01B 3/32; C10L 3/00; Y02C 10/08; Y02C 10/00; Y02C 10/14

USPC ............................................ 568/840; 95/139
See application file for complete search history.

(56) References Cited

U.S. PATENT DOCUMENTS

| | | |
|---|---|---|
| 5,928,806 A | 7/1999 | Olah et al. |
| 7,378,561 B2 | 5/2008 | Olah et al. |
| 7,459,590 B2 | 12/2008 | Olah et al. |
| 7,605,293 B2 | 10/2009 | Olah et al. |
| 7,608,743 B2 | 10/2009 | Olah et al. |
| 7,705,059 B2 | 4/2010 | Olah et al. |
| 7,795,175 B2 | 9/2010 | Olah et al. |
| 7,846,978 B2 | 12/2010 | Olah et al. |
| 2006/0235088 A1 | 10/2006 | Olah et al. |
| 2006/0235091 A1 | 10/2006 | Olah et al. |
| 2007/0254969 A1* | 11/2007 | Olah ........................ C07C 1/20 518/726 |
| 2008/0001225 A1 | 1/2008 | Furukawa et al. |
| 2008/0039538 A1* | 2/2008 | Olah et al. ................ 518/702 |
| 2008/0220480 A1 | 9/2008 | Olah et al. |
| 2008/0319093 A1* | 12/2008 | Olah ........................ C01B 3/38 518/700 |
| 2009/0030240 A1 | 1/2009 | Olah et al. |
| 2009/0100754 A1* | 4/2009 | Gil ............................ 48/201 |
| 2009/0145843 A1 | 6/2009 | Ahner |
| 2009/0285739 A1 | 11/2009 | Olah et al. |
| 2009/0293348 A1 | 12/2009 | Olah et al. |
| 2010/0120104 A1 | 5/2010 | Reed |
| 2010/0152474 A1 | 6/2010 | Olah et al. |
| 2011/0086928 A1 | 4/2011 | Olah et al. |

FOREIGN PATENT DOCUMENTS

| | | |
|---|---|---|
| WO | 2008/021698 A2 | 2/2008 |
| WO | 2009/140478 A2 | 11/2009 |

OTHER PUBLICATIONS

International Search Report, PCT/US2011/050969, mailed Apr. 25, 2012.

* cited by examiner

*Primary Examiner* — Jafar Parsa
*Assistant Examiner* — Amy C Bonparte
(74) *Attorney, Agent, or Firm* — Winston & Strawn LLP

(57) ABSTRACT

A method for recycling a carbon-containing greenhouse gas emissions such as carbon dioxide and methane (natural gas) or a hydrocarbon homolog thereof. The method includes the steps of capturing the emissions, sequestering them in an underground or undersea storage area, withdrawing them from the storage area after storage therein, and converting them to carbon-containing compounds such as methanol, dimethyl ether and derived products. Greenhouse gases such as carbon dioxide and methane are chemically recycled to provide a permanent and inexhaustible supply of carbon-containing fuels or products, which subsequently can be combusted or used without increasing the carbon dioxide content of the atmosphere. The method is thus effective in neutralizing or reducing the carbon footprint due to human activities related to combustion or use of carbon-containing fuels while providing a repeatedly sustainable carbon source.

16 Claims, No Drawings

RECYCLING CARBON DIOXIDE VIA CAPTURE AND TEMPORARY STORAGE TO PRODUCE RENEWABLE FUELS AND DERIVED PRODUCTS

FIELD OF THE INVENTION

The invention relates to recycling of sequestered carbon-containing gases by converting the gases to renewable fuels such as methanol and dimethyl ether, and products derived therefrom.

BACKGROUND

A major environmental concern today is the increase of the "carbon footprint" of human activities. The "carbon footprint" is the amount of carbon dioxide ($CO_2$) produced by an entity due to the use of carbon-containing fuels or the like. The carbon dioxide that is inevitably formed from the combustion or degradation of carbon-based fuels, materials or any live processes is a major concern because it contributes significantly to the change of our climate by causing harmful global warming. When any carbon-containing compound is combusted or degraded, carbon dioxide is formed. Carbon dioxide is an environmentally harmful greenhouse gas. The use of coal or other fossil fuels, and power plants burning such fuels, cement plants, breweries, transportation sector, etc., produce annually in excess of 30 billion tonnes of carbon dioxide. Various other activities such as agriculture, live processes and discharge of varied natural sources also produce large amounts of carbon dioxide. While as much as half of the carbon dioxide related to human activities is absorbed or recycled by nature, such as the oceans and photosynthesis processes, the remaining amount still greatly overloads and upsets the terrestrial carbon dioxide balance.

One of the current major challenges for humankind is how to dispose of such harmful excessive greenhouse carbon dioxide emissions to mitigate their contribution to global climate change (or global warming). The Kyoto and Copenhagen international conferences attempted to find solutions to limit $CO_2$ emission due to the excessive burning of fossil fuels or other anthropogenic activities but resulted only in regulatory and economic (carbon quotas, taxes, cap and trade) approaches. Also, widespread efforts are being made to try to reduce the use of carbon-containing fuels and materials and to replace fossil fuels with non-carbon-containing energy sources. It is recognized that non-carbon-containing sources of energy, such as alternative sources, e.g., hydro, geothermal, solar, wind, as well as others, and atomic energy should be used more. Further, an essential aspect of our carbon future is the fact that fossil fuel resources are limited and will be used up by increasing demand of population growth and industrialization. Relatively easily accessible oil and natural gas may only last this century, whereas more abundant coal another two centuries. In the foreseeable future, however, fossil energy sources will continue to be utilized because of its ready availability and relatively low cost compared to the alternatives. Thus, the need remains for disposal of such emissions.

One way to address the harmful effects of human-generated carbon dioxide emissions is the capture and sequestration (or storage) of carbon dioxide in depleted oil and gas fields or coal mines, at the bottom of the sea or underground in caverns or other sealed cavities. This is generally referred to as carbon capture and sequestration ("CCS"). There are, however, obvious limitations of this approach. Sequestration is a costly process that does not provide any economic benefit and at best is only a temporary solution. Volatile carbon dioxide can leak out from subterranean or under-the-seas storage facilities even in the best selected geological formations and location, such as depleted oil fields or the bottom of the seas or lakes. Sequestered (or stored) carbon dioxide also is very susceptible to geological disturbances, such as earthquakes, slides, and volcanic eruption. Geological disturbances can cause the instant release of huge amounts of stored carbon dioxide on a massive scale and have a deadly effect, since carbon dioxide is heavier than the air and can suffocate living creatures in the proximity of large scale releases of carbon dioxide. Also, even if stored carbon dioxide does not leak and converts to carbonates over time (which is how limestone is formed in nature over eons), the extremely long time needed for such carbonation renders carbon dioxide sequestration only a temporary storage solution on the human time scale. Furthermore, CCS renders a significant part of the Earth's carbon resources lay dormant and of little use. Thus, improved solutions to address and reduce carbon dioxide emissions are needed.

SUMMARY OF THE INVENTION

The invention relates to a method for recycling a carbon-containing exhausts such as carbon dioxide or methane or its homologs after their capture and sequestration (CCS) making them renewable while at the same time mitigating their environmental harm. The method comprises withdrawing the carbon containing gas from the storage or sequestration points and converting them to carbon-containing fuels and compounds. The method provides a safe, environmentally adoptable renewable energy source. The carbon-containing compounds are preferably synthetic hydrocarbons, such as methanol, dimethyl ether, or derivatives thereof. By converting such stored gas into carbon-containing fuels and compounds, there becomes less of a concern of the unintended escape of gas that could occur if the gas were otherwise subjected to such long term storage.

In an embodiment, the recycled carbon-containing gas is carbon dioxide emissions produced by the combustion or use of carbon-containing fuel, or carbon dioxide captured from flue or off-gases of coal or other fossil fuel burning plants, geothermal power facilities, cement, aluminum or other industrial plants or factories, industrial or agricultural wastes or byproducts of natural gas production. The recycled gas can also be carbon dioxide captured from the air or atmosphere, such as by adsorption on an adsorbent followed by treatment, e.g., heating, of the adsorbent to release the adsorbed carbon dioxide.

In an embodiment, carbon dioxide is captured and recycled to produce methanol by any suitable method such as by hydrogenative reductive processes. Methanol can be further reacted or processed to form dimethyl carbonate or dimethyl ether. Methanol and dimethyl ether also can be converted to ethylene or propylene by acidic-basic or zeolitic catalysis. Ethylene and propylene, in turn, can be converted to any hydrocarbon products such as ethanol, propanol or isopropanol, or higher olefins, or aromatics, or products therefrom, such as for use as feedstocks for chemicals or as transportation fuels. These can replace fossil fuel derived transportation and industrial fuels and feed-stocks.

The invention also relates to recycling carbon-containing gases to control or reduce the overall carbon footprint of the planet. Thus, the current lifestyles that rely extensively on conventional carbon containing fuels and products can continue indefinitely by substituting the new carbon-containing compounds or products obtained by recycling of carbon-containing gases without harming the environment to preserve and even improve the atmosphere for the benefit of future generations.

Another embodiment of the invention relates from moving from CCS to carbon capture and recycling ("CCR") for producing methanol from carbon dioxide or methane gas (which is also a potential greenhouse gas with global warming potential 23 times that of $CO_2$) from a sequestered supply in an underground storage facility avoiding escape of the gas from the underground storage facility.

Also, the invention relates to the use of a supply of carbon dioxide or methane gas which is sequestered in an underground storage facility for the production of methanol to recycle the gas into a useful product while avoiding escape of the gas from the underground storage facility.

DETAILED DESCRIPTION OF THE PREFERRED EMBODIMENTS

As used herein, the term "carbon footprint" is a measure of the impact human activities have on the environment in terms of the amount of green house gases produced, measured in units of carbon dioxide. Thus, the carbon footprint is a measure of the excess global amount of carbon dioxide and other carbon-containing greenhouse gases emitted by an entity or accumulated over the full life cycle of a product or service. It is a useful measure for conceptualizing an entity's impact in contributing to global warming. A related conceptual tool is the "carbon offset," which indicates the mitigation of carbon emissions through the development of alternative carbon sources such as solar or wind energy or through carbon recycling by biological process such as reforestation.

An "entity" can be an individual, household or other group of people, or an organization such as a company. An entity generates or is capable of generating carbon footprint due to the combustion of fossil fuel, industrial activities, or fine process of other generation of carbon dioxide.

Normally, the carbon footprint is expressed as a $CO_2$ equivalent (usually in kilograms or tonnes), which accounts for the same global warming effects of different greenhouse gases. Carbon footprints can be calculated from all carbon dioxide sources or can be restricted to the main source of carbon dioxide, which is that generated from the use of fossil fuels, industrial and like processes. Carbon footprints can be calculated to include only direct emissions (typically from energy used in the home, workplace, transportation, e.g., travel by cars, airplanes, rail and other transportation), or also to include indirect emissions (including $CO_2$ emissions as a result of goods and services consumed).

The present invention provides an efficient and permanent way to control, neutralize or reduce carbon footprints without limiting or prohibiting the use of carbon-containing fuels, materials or products that leave carbon footprints.

Also, the present invention discloses a new solution to the problems of carbon dioxide emissions and temporary CCS. It is based on the realization that not unlike other elements, which are essential sources for terrestrial life, such as water ($H_2O$), a source of hydrogen and oxygen, atmospheric nitrogen, and natural sources for carbon (carbon dioxide) as well as methane and other hydrocarbon sources are recycled by nature over various periods of time. This new technology can supplement and greatly accelerate nature. A well-known analogy is the Haber-Bosch recycling of atmospheric nitrogen to ammonia and derived products. Carbon recycling is carried out by nature's photosynthetic cycle capturing $CO_2$ from the air by living organisms essential for terrestrial life. However, renewal of natural fossil fuels from natural sources is a very slow process, taking many millions of years, which is too long for mankind to wait.

There is clearly a need to supplement nature's slow regeneration of fossil fuel resources. Plants, crops, vegetation and ecosystems efficiently recycle carbon dioxide to new bio-systems containing carbohydrates, proteins, cellulosic materials and varied life forms. Their conversion to carbon fuels, however, competes with essential food production and necessitates vast agricultural land, water and other land resources (including forests, remaining wilderness, etc.) greatly limiting the ability of biofuels to supplant fossil fuels.

A feasible way of chemical carbon recycling of carbon dioxide or CCR derived from natural or industrial sources is to react the carbon dioxide with hydrogen derived from water using any available source of energy, and preferentially using solar or other alternate energy or atomic energy. Carbon dioxide emissions are increasingly stored underground or under the seas and this provides a plentiful supply of carbon dioxide for such reactions. Thus, the present invention now fills an essential gap in making the chemical carbon cycle practical by combining carbon capture and optional storage by the permanent process of subsequent chemical recycling of withdrawal of stored carbon dioxide to form hydrocarbon fuels and derived products. This renders carbon dioxide a renewable inexhaustible carbon source while also mitigating the environmentally harmful build up of excessive $CO_2$ emissions.

One embodiment of the present invention relates to the new use of captured and temporarily stored carbon dioxide or methane (as well as of any other hydrocarbon sources) as withdrawable raw materials for their conversion to methanol, dimethyl ether (DME) and derived products. This process uses the chemical approaches to produce methanol and its derived products and materials as disclosed, e.g., in U.S. Pat. Nos. 7,605,293 and 7,608,743. This new approach combines temporary carbon capture and storage with recycling to make carbon containing fuels and products renewable in an environmentally carbon neutral way. It also provides a feasible economic and safe way to mitigate the environmentally harmful effects of carbon dioxide, considered until now only a harmful greenhouse gas, as an inexhaustible carbon source of the future. This is an alternative or adjunct to the capture and recycle of atmospheric carbon dioxide disclosed for example in U.S. Pat. Nos. 7,378,561 and 7,459,590. All of these can be used to provide an inexhaustible carbon source for future generations. Consequently, dependence on fossil fuels will be replaced by economical and efficient chemical carbon recycling.

Thus, the invention provides a process in which a captured or sequestered carbon-containing gas, such as carbon dioxide, after temporary storage, is withdrawn for chemical recycling. The withdrawn carbon-containing gas is chemically recycled by being converted into carbon-containing compounds such as methanol, dimethyl ether (DME), or their derived chemical products.

In another embodiment, the carbon-containing gas that is recycled according to the invention is methane or other hydrocarbon homologs thereof. These homologs include natural gas as well as other low carbon number hydrocarbon gases which, as exemplified by methane, can be oxidatively converted to methanol. Methane from any source can be used, e.g., methane trapped as hydrates (gas hydrates) in nature or produced by other natural or anthropogenic activities (e.g., agriculture and animal husbandry).

The carbon-containing gas that is captured is preferably separated and, when necessary, purified from accompanying toxic or other harmful impurities by any known and suitable method. For example, the carbon-containing gas can be separated using nanostructured, supported polymeric absorbents containing alkanolamine or nitrogen, such as polyethyleneimine, as described in U.S. Pat. No. 7,795,175.

The carbon-containing gas that is sequestered (or stored) in any suitable underground cavity or facility. For example, the carbon-containing gas can be sequestered in depleted oil fields, coal beds, or other suitable geological formations. The carbon-containing gas also can be compressed and injected into the depths of the sea or lake for storage.

After sequestration and temporary storage in an underground facility, the carbon-containing gas is accessed and withdrawn from the storage facility for subsequent chemical recycling. The withdrawal can be effected by any known and suitable method. For example, the gas can be withdrawn by raising the temperature and/or decreasing the pressure. The withdrawn gas is transported by suitable transportation (e.g., pipelines, ships, railroads, trucks, etc.) to a recycling facility. The withdrawn carbon-containing gas is then is converted to carbon-containing compounds by any known and suitable conversion reactions. For example, the gas is converted to methanol, dimethyl ether, or products derived therefrom by hydrogenative ($CO_2$) or oxidative ($CH_4$) conversions.

The energy needed for the overall process can be obtained from any source, including fossil fuels, any alternative energy sources (e.g., solar, wind, geothermal, hydro, etc.), and atomic energy. Thus, the present process allows safe use of carbon fuels to generate electricity, while also providing a means for efficient storage of energy, including electricity on a large scale. When alternative energy sources are used, the process provides further environmental benefits.

The carbon-containing gas to be sequestered and stored can be obtained from any suitable or desired source. For example, carbon dioxide can be captured from flue or off-gases of coal or other fossil fuel burning plants, geothermal power facilities, cement, aluminum or other industrial plants or factories, breweries, industrial or agricultural wastes, or byproducts of natural gas production. Carbon dioxide also can be captured and removed from the air or atmosphere by absorbing it onto a suitable adsorbent followed by heating or otherwise treating the adsorbent to release the adsorbed carbon dioxide therefrom.

By combining sequestration with subsequent withdrawal and recycling, the invention removes the drawbacks of sequestration, while also providing a safe, inexhaustible and storable carbon reserve for future use, thereby supplementing nature's own photosynthetic carbon cycle. The invention thus provides an efficient and convenient way of storing and subsequently recycling greenhouse gases such as carbon dioxide from natural and industrial sources including carbon dioxide emissions from fossil fuels and excessive carbon dioxide in the atmosphere, for a feasible technical carbon cycle.

Further, the chemical recycling of carbon-containing emissions according to the invention mitigates the environmentally harmful effects of greenhouse gases, e.g., carbon dioxide emissions, by achieving neutral or negative carbon footprint. For example, neutral or negative carbon footprint is achieved by recycling higher concentrations of industrial and natural carbon dioxide sources and emissions, and/or by capturing and recycling an equivalent or greater amount of carbon dioxide directly from the atmosphere. By first capturing carbon dioxide from the environment or preventing carbon dioxide from being discharged into the environment, and then converting the captured carbon dioxide to carbon-based fuel or feedstock, fuel or feedstock can be provided in an environmentally beneficial manner, without increasing carbon dioxide emissions or carbon footprint. In a further embodiment, fuel or feedstock, and/or products made therefrom that are produced by the present recycling method also can be used in an environmentally neutral manner.

In a preferred embodiment, carbon dioxide is chemically recycled to produce alternative energy sources, such as methanol, DME and their products. Methanol and DME are well known fuels, but also are suitable as energy storage and building blocks for various synthetic products and materials, including proteins.

For example, carbon dioxide that is captured and recovered according to the invention can be used to produce methanol or DME, and their derived products and materials, as disclosed in U.S. Pat. Nos. 5,928,806; 7,605,293; and 7,608,743, and U.S. Pat. Appln. Pub. Nos. 2006/0235088, 2008/0319093, 2008/0001225, and 2009/0030240, the entire content of each of which is expressly incorporated herein by reference.

In an embodiment, carbon dioxide captured, sequestered, and then chemically recycled into methanol by suitable hydrogenative reductive processes. Other products, such as dimethyl carbonate, can be formed by reacting the methanol with phosgene or by oxidative carbonylation of methanol. In an example, the methanol produced according to the invention is dehydrated to DME, which in turn can be used as a starting material for additional products. Dimethyl ether can be used as a substitute for natural gas and LPG, e.g., for heating for households or industrial use. Also, dimethyl ether can be heated in the presence of an acidic-basic or zeolitic catalyst to form ethylene or propylene, which can then be converted either to higher olefins, synthetic hydrocarbons or aromatics and their products, for use as feedstocks for chemicals or as transportation fuels. Ethylene or propylene can be hydrated to form ethanol or propanol, e.g., isopropanol. These carbon based fuels and products can be conventionally combusted or utilized without increasing the carbon footprint of any individuals or entities and without causing any further harm to the atmosphere by emitting any further carbon dioxide.

All these processes are generally known from the prior patent documents mentioned herein, but the generation of fuels and products from sequestered carbon dioxide is a novel concept that will prevent further environmental damage while not requiring reduced use of carbon-based materials or changed lifestyle.

The present invention thus achieves mitigation of the harmful generation of carbon dioxide that adds to the carbon footprint of human activities by utilizing sequestered carbon dioxide and chemically recycling it, preferably by using a suitable form of conversion to methanol or dimethyl ether, making the human carbon footprint neutral or even negative. The materials produced through the present chemical recycling of carbon dioxide can then be used as convenient energy source or medium and in various uses, e.g., transportation materials, fuels (including for internal combustion or fuel cells), household and industrial gases (for heating, cooking, etc.), and renewable raw materials for producing synthetic hydrocarbons and their products. By mitigating the harmful excessive carbon footprint of human activities, no excessive carbon dioxide is released into the atmosphere, allowing the continued environmentally friendly renewable use of carbon-containing fuels and materials while also diminishing or neutralizing the harmful environmental effect of excessive carbon dioxide discharge into the atmosphere that causes global warming. At the same time, the invention also provides an inexhaustible, renewable and environmentally benign carbon source, namely, carbon dioxide, that is the starting point for making the fuels and products that are heavily and commonly used.

The invention also provides a method for controlling, neutralizing or decreasing the human carbon footprint of an entity, which comprises capturing and sequestering a carbon containing gas in an underground or undersea storage area; withdrawing the gas from the storage area after sequestration or storage therein; and converting the gas to a carbon-containing compound to provide a renewable energy source while avoiding any unintended escape of the gas from the storage area and while controlling, neutralizing or decreasing the carbon footprint of the entity. The entity can be a power plant or other facility, which generates carbon dioxide emissions, with the emissions gas captured and sequestered in the underground or undersea area. Thereafter, the gas is accessed and withdrawn for use as a reactant as described herein. The resulting carbon containing compound(s) can be used as an energy source in the power plant itself, with the emissions captured and returned to the storage area. This results in a renewable and reusable energy source that will never be exhausted and which does not contribute to or add to the carbon dioxide content of the atmosphere, thus benefitting future generations.

EXAMPLES

The preceding description and the following examples are illustrative only and are not to be considered as restrictive or limiting of the invention.

Example 1

Industrial or naturally released carbon-containing greenhouse gases, primarily carbon dioxide or methane (or its homologs), are captured and separated. $CO_2$ can be separated using suitable adsorbents including nanostructured, supported polymeric absorbents containing alkanolamine or nitrogen, such as polyethyleneimine. The gases are purified from accompanying toxic or other harmful impurities by a purification method.

The separated greenhouse gases are then sequestered (stored) in suitable underground facility, such as depleted oil fields, coal beds or other suitable geological formations. Alternatively, the carbon containing gases are compressed and injected into the depths of the sea or lake for storage.

The stored carbon dioxide or methane is withdrawn from the storage facility by raising the temperature or decreasing the pressure. The carbon dioxide can be withdrawn from the same pipelines used to introduce the carbon dioxide into the cavern. The withdrawn carbon dioxide or methane is transported to a recycling facility, and then is converted by hydrogenative ($CO_2$) or reformative ($CH_4$) conversions, to methanol, DME, or their derived products.

Example 2

Stored methane or natural gas (or related hydrocarbons) is withdrawn and is combined with $CO_2$ by the dry or bireforming methods to make methanol, dimethyl ether or related products. The processing methods are described in US Patent Applications 2008319093 and 2009030240. For example, methane or natural gas can be used as the hydrogen source in the reductive conversion of carbon dioxide (dry reforming) or using a suitable combination with steam reforming (wet reforming) to provide a 1:2 molar mixture of carbon monoxide and hydrogen, which subsequently can react to produce methanol and derived products.

What is claimed is:

1. A method for controlling, neutralizing or decreasing the human carbon footprint of an entity by recycling and converting carbon dioxide gas emissions which have been generated by the entity but which are captured and sequestered in a storage area comprising a geological formation located underground or undersea, wherein the method comprises withdrawing the gas by accessing the gas in the storage area and removing the gas from the storage area by raising the temperature or decreasing the pressure in the storage area so that the carbon dioxide can be withdrawn from the storage area; and converting all of the withdrawn gas to methanol by hydrogenative reductive processes to provide a renewable energy source while also avoiding any escape or release of the gas from the storage area into the atmosphere, thus controlling, neutralizing or decreasing the carbon footprint of the entity by converting all of the withdrawn carbon dioxide emissions to methanol.

2. The method of claim 1, wherein the renewable energy source of methanol is used as a carbon-containing fuel or to form another compound or further product.

3. The method of claim 2, wherein the methanol is used as is or is converted to dimethyl ether, or products derived therefrom.

4. The method of claim 1, wherein the withdrawn carbon-dioxide gas is subjected to dry reforming or to combined dry reforming and wet reforming (bireforming) to provide a 1:2 molar mixture of carbon monoxide and hydrogen, which subsequently reacts to produce exclusively methanol.

5. The method of claim 1, wherein the carbon dioxide is emitted from combustion or use of a carbon-containing fuel before being sequestered or stored in the storage area.

6. The method of claim 1, wherein the carbon dioxide is captured from flue or off-gases of coal or other fossil fuel burning plants, geothermal power facilities, cement, aluminum or other industrial plants or factories, industrial or agricultural wastes or byproducts of natural gas production before being sequestered or stored in the storage area.

7. The method of claim 3, which further comprises forming dimethyl carbonate by reaction of the methanol with phosgene or by oxidative carbonylation of the methanol.

8. The method of claim 3, which further comprises dehydrating the methanol under conditions sufficient to produce dimethyl ether.

9. The method of claim 8, wherein the dimethyl ether is used as a substitute for diesel fuel, natural gas or LPG for household heating.

10. The method of claim 3, which further comprises converting the methanol or dimethyl ether to ethylene or propylene in the presence of a suitable catalyst.

11. The method of claim 10, which further comprises converting the ethylene or propylene to higher olefins, synthetic hydrocarbons or aromatics, or products therefrom, for use as feedstocks for chemicals or as transportation fuels.

12. The method of claim 10, which further comprises hydrating the ethylene or propylene to form ethanol, propanol or isopropanol.

13. In a method for controlling, neutralizing or decreasing the human carbon footprint of an entity by recycling and converting carbon dioxide gas emissions to produce methanol from a feed gas of carbon dioxide, methane, natural gas or a hydrocarbon homolog thereof, the improvement which comprises obtaining all of the carbon dioxide for the feed gas from a sequestered supply, wherein the carbon dioxide has been generated by the entity and then captured and sequestered in a storage area comprising a geological formation located underground or undersea by delivery through pipelines to the storage area, and removing the carbon dioxide from the sequestered supply by accessing the gas in the storage area through the same pipelines used to introduce the carbon dioxide therein by raising the temperature or decreasing the pressure in the storage area with the removed gas used as a reactant to form the methanol by hydrogenative reductive processes or to convert the methanol into carbon-containing compounds derived therefrom in order to provide a renewable energy source, wherein all removed gas is used as a reactant in order to avoid any escape of the gas from the storage area into the atmosphere, thus controlling, neutralizing or decreasing the carbon footprint of the entity by converting all of the withdrawn carbon dioxide emissions to methanol.

14. The method of claim 4 which further comprises providing solar, atomic or other alternative energy sources for the preparation of methanol by the dry or dry and wet reforming reactions.

15. The method of claim 13 which further comprises providing solar, atomic or other alternative energy sources for the preparation of methanol by reacting the withdrawn carbon dioxide gas with hydrogen derived from water.

16. The method of claim 13, wherein the withdrawn carbon-dioxide gas is subjected to dry reforming or to combined dry reforming and wet reforming (bireforming) to provide a 1:2 molar mixture of carbon monoxide and hydrogen, which subsequently reacts to produce exclusively methanol.

\* \* \* \* \*